(12) United States Patent
Zancho et al.

(10) Patent No.: US 7,874,983 B2
(45) Date of Patent: Jan. 25, 2011

(54) DETERMINATION OF EMOTIONAL AND PHYSIOLOGICAL STATES OF A RECIPIENT OF A COMMUNICATION

(75) Inventors: William Zancho, Hawthorn Woods, IL (US); Sreeram Balakrishnan, Los Altos, CA (US); Kenneth Douros, South Barrington, IL (US); Robert Gardner, Gilbert, AZ (US); Sowmyan Ranganathan, Lombard, IL (US)

(73) Assignee: Motorola Mobility, Inc., Libertyville, IL (US)

( * ) Notice: Subject to any disclaimer, the term of this patent is extended or adjusted under 35 U.S.C. 154(b) by 0 days.

(21) Appl. No.: 10/351,706

(22) Filed: Jan. 27, 2003

(65) Prior Publication Data

US 2004/0147814 A1 Jul. 29, 2004

(51) Int. Cl.
A61B 5/00 (2006.01)
(52) U.S. Cl. ........................ 600/300; 128/920; 434/236
(58) Field of Classification Search ......... 600/300–301; 128/903–905, 920–925; 455/118; 705/2–4
See application file for complete search history.

(56) References Cited

U.S. PATENT DOCUMENTS

| | | | |
|---|---|---|---|
| 5,630,159 A | 5/1997 | Zancho | |
| 5,633,484 A | 5/1997 | Zancho et al. | |
| 5,814,798 A | 9/1998 | Zancho | |
| 6,064,383 A | 5/2000 | Skelly | |
| 6,069,622 A | 5/2000 | Kurlander | |
| 6,157,624 A | 12/2000 | Zancho | |
| 6,302,844 B1 * | 10/2001 | Walker et al. | 600/300 |
| 6,459,913 B2 | 10/2002 | Cloutier | |
| 6,569,094 B2 * | 5/2003 | Suzuki et al. | 600/300 |
| 6,817,979 B2 * | 11/2004 | Nihtila | 600/300 |
| 2001/0049596 A1 | 12/2001 | Lavine et al. | |
| 2002/0077135 A1 | 6/2002 | Hyon | |
| 2002/0087649 A1 | 7/2002 | Horvitz | |
| 2002/0143241 A1 | 10/2002 | Thorell | |
| 2002/0154010 A1 | 10/2002 | Tu et al. | |
| 2002/0197967 A1 * | 12/2002 | Scholl et al. | 455/118 |
| 2003/0131143 A1 | 7/2003 | Myers | |
| 2003/0149978 A1 | 8/2003 | Plotnick | |
| 2004/0209600 A1 | 10/2004 | Werner et al. | |

FOREIGN PATENT DOCUMENTS

WO WO 02/44991 A1 6/2002
WO 2006065637 A2 6/2006

OTHER PUBLICATIONS

U.S. Appl. No. 08/366,123, entitled "Method and Apparatus for Personal Attribute Selection and Management Using Prediction", Abandoned.

\* cited by examiner

*Primary Examiner*—Henry M Johnson, III
*Assistant Examiner*—Kai Rajan

(57) ABSTRACT

A communication device capable of determining an emotional or physiological state of a user of the device includes an input device that provides a signal indicative of one of an emotional and a physiological state of a user of the device. A controller receives the signal from the input device and interprets the signal into state data identifying one of an emotional and a physiological state of a user of the device. The device makes the state data available to be downloaded such that a device sending a communication can appropriately adapt its communication method and transport mode of user interface to suit the recipient's condition.

22 Claims, 5 Drawing Sheets

DETERMINATION OF EMOTIONAL AND PHYSIOLOGICAL STATES OF A RECIPIENT OF A COMMUNICATION

FIELD OF THE INVENTION

The present invention relates to communication formatting and, more particularly, relates to a determination of a state of a user and an adaptation of a communication thereto.

BACKGROUND OF THE INVENTION

As technology increases, people are having more and more interactions using many different communication devices. These interactions occur in many different situations where a user may be in a more or less communicative mood, depending on their emotional or physiological state at any particular time. An individual tends to be more open and communicative if they are in a good mood or not under stress, and less open and communicative if they are in a bad mood or under stress. In the latter case, communication is less efficient.

One prior art technique allows a user to store communication and interface preferences in a memory that can be accessed and used to configure a user interface during a communication. Although an improvement in the art, this technique does not account for emotional or physiological information to be provided to a sender of information or to the originator of a voice call. Rather, this technique is concerned with hardware and software configurations of the user interface and its modalities.

Another prior art technique allows a user to send emotional information as part of a communication. However, this technique requires an active input of information by a user, and does not provide a method for a sender of information to obtain an emotional or physiological state of a recipient of the information before sending such information or making such voice call.

These examples also require a recipient to actively program preferences or provide emotional information into their communication equipment, or provide some other kind of active input. No mechanism exists to establish an emotional or physiological state of a recipient of a communication by the sender of such communication.

What is needed is a way for a sender of information to determine emotional or physiological states of a recipient of the information, and adapt a human communication interaction accordingly. It would also be of benefit if these states can be provided automatically without any action on the part of the recipient or sender of the information or initiator of the call. It would also be an advantage if a sending device could determine the state of a recipient through the recipient's communication device before the start of a communication to enable the appropriate form of communication and the appropriate modality of machine-to-human interaction.

BRIEF DESCRIPTION OF THE DRAWINGS

The features of the present invention, which are believed to be novel, are set forth with particularity in the appended claims. The invention, together with further objects and advantages thereof, may best be understood by making reference to the following description, taken in conjunction with the accompanying drawings, in the several figures of which like reference numerals identify identical elements, wherein:

DETAILED DESCRIPTION OF THE PREFERRED EMBODIMENTS

The foregoing and other problems can be solved by the apparatus, method and system of the present invention. A sender (call originator) or sending device of information is able to determine emotional or physiological states of a recipient of the information and adapt a communication to be sent to the recipient accordingly. The sending individual can elect to originate the communication in this mode or defer to a time when the psychophysiological state of the target individual enables the mode the sender prefers. Such states can be stored in the recipient device autonomously and accessed in real time by any sender of information before the actual communication is initiated. The recipient device can include sensors or other input devices to actively or passively detect the emotional or physiological state of an operator of the device. The input of the psychophysiological information can be either sensed without user action or through intentional user action, such as squeezing the phone, for example. This state information can be exchanged either one-way or two-way, and a communication can be adapted accordingly, using either manual or automatic techniques. Recipient states can thus be conveniently established and used such that information for a recipient can be readily modified to communicate in the most efficient manner possible, given the emotional or physiological state of the recipient.

Advantageously, the present invention provide a mechanism to capture, characterize, transfer to another and interpret, a user's emotional and physiological state through a protocol that enables the sender of information or initiator of communication to understand the state of the recipient and their associated context during the communication, enabling the sender's communication device to adapt his communication accordingly. The present invention also indicates to the sender the interface mode of the receptor so that the sender has its expectations controlled for a response or to elect to defer the communication if preferred. Similarly, the present invention enables the intended recipient to also know the state of the sender. The present invention enables superior dialogue with or without the physical presence of the communicating parties, by providing a classification of emotions, etc. This can be accomplished through storage of preferred communication transmission and reception modes of interaction when specific emotional states occur.

Figure 1:
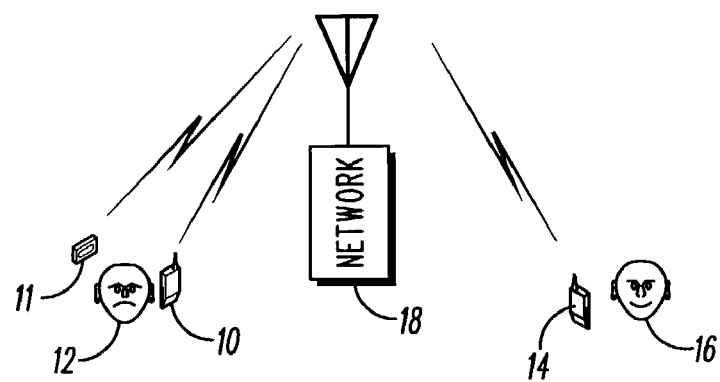
FIG. 1 illustrates a simplified communication system for determining the emotional and physiological state of a recipient of a communication, in accordance with the present invention.

FIG. 1 illustrates a communication device 10 such as a cellular telephone capable of determining an emotional and/or physiological state of a user 12 of the communication device 10. It should be recognized that the communication device 10 can also be a mobile device, pager, cordless telephone, corded telephone, computer, personal digital assistant, or any other type of communication device. The communication device is capable of communication with any other communication device 14 and associated user 16 through an existing or future network interface 18, including direct point-to-point connection. For example, the communication can be transmitted over a cellular digital packet data (CDPD) or short message service (SMS) on an existing analog advanced mobile phone (AMPS) service or over point-to-point and push-to-talk services. The communication can also be transmitted in a data format of the Global System for Mobile communications (GSM) system or a time division multiple access (TDMA) system or code division multiple access (CDMA) system. A worldwide satellite network, Internet network, wide area network, and local area network can also be used for the network 18.

In the context of the present invention, user 12 will be referred to as the recipient of information, user 16 as the sender of information, device 10 as a receiving communication device, and device 14 as a sending communication device. However, it should be recognized that these roles easily can be reversed such that the present invention operates in a two-way mode. In particular, a device can act as both a sender and recipient device at the same time In operation, the present invention describes a system wherein the sending communication device 14 is capable of adapting an outgoing communication in accordance with data defining a determined emotional and/or physiological state of an intended recipient 12. The receiving communication device 10 is capable of relating determined emotional and physiological state data of the user 12 to the sending communication device 14 and user 16. The devices communicate over a network 18 using one or more communication protocols. In response to receiving the state data, the sending device can change the format or protocol of the information to be sent to the recipient. For example, the sending device 14 can send information in a different format and protocol to a paging device 11 of the user 12 to better adapt to the state of the user 12. Alternatively, the information can still be sent to the recipient device 10 albeit in a different format or interface mode more suited to the state of the user 12.

Figure 2:
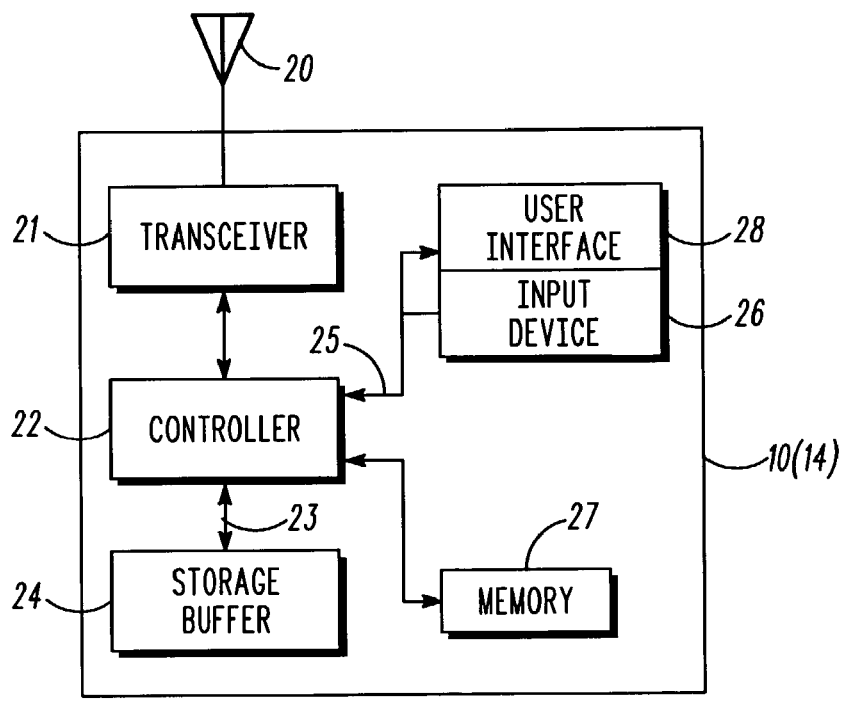
FIG. 2 illustrates schematic block diagram of a communication device, in accordance with the present invention.

Referring to FIG. 2, the communication device 10 is typically a cellular telephone with an internal bus for connection of the internal components of the cellular telephone together and to the user interface 28 and input device 26. The internal bus is under control of a central processing unit (CPU) or controller 22. A memory 27 with radiotelephone control software connects to the internal bus and provides control of the functionality of the cellular telephone. A radio RF subsystem connects to an antenna 20 via a transceiver 21. The radio subsystem is operated according to standard cellular telephone air interface specifications under control of the radiotelephone control software memory. The user interface 28 is also operated over the internal bus of the cellular telephone and includes input and output devices such as a microphone, a speaker, a keyboard and a display that are not shown for simplicity.

The recipient communication device 10 (and/or 14) includes an input device 26 that is used to detect the emotional arid/or physiological state of the user of the device 10. In practice, these states include one or more of a biological process of the recipient, an environment of the recipient, and a context of the recipient. Specifically, the input device 26 can include one or more of the group of a biosensor, an environmental monitor, a voice analyzer, a pressure sensor, an optical analyzer, a download of a workload schedule of the user, and any other ways to convey an emotional or physiological state of a user. Using any of these means, the input device 26 provides a signal 25 indicative of one of an emotional and a physiological state of a user of the device.

The controller 22 of the device 10 is coupled to the input device 26 and inputs the signal 25 from the input device 26. The controller 22 is also coupled to a storage buffer 24. The controller 22 interprets the signal 25 into state data 23 identifying one of an emotional and a physiological state of a user of the device 10. The controller 22 can then store the state data 23 in the buffer 24, where the state data 23 is available to be used to set the communication method and user interface modes and to indicate to a sender, through the transceiver circuitry 20, 21 of the device 10, the methods and modes which will be used. The input device 26 can include an existing user interface 28 of the device 10. Through the user interface 28, a user can directly supply communication preferences to the controller 22 defining an emotion, physiological or other state, or the controller 22 can act autonomously to interpret the state data 23 from the signal 25 of the input device 26. Preferably, the controller and input device dynamically monitor the emotional and physiological state of the user.

Figure 3:
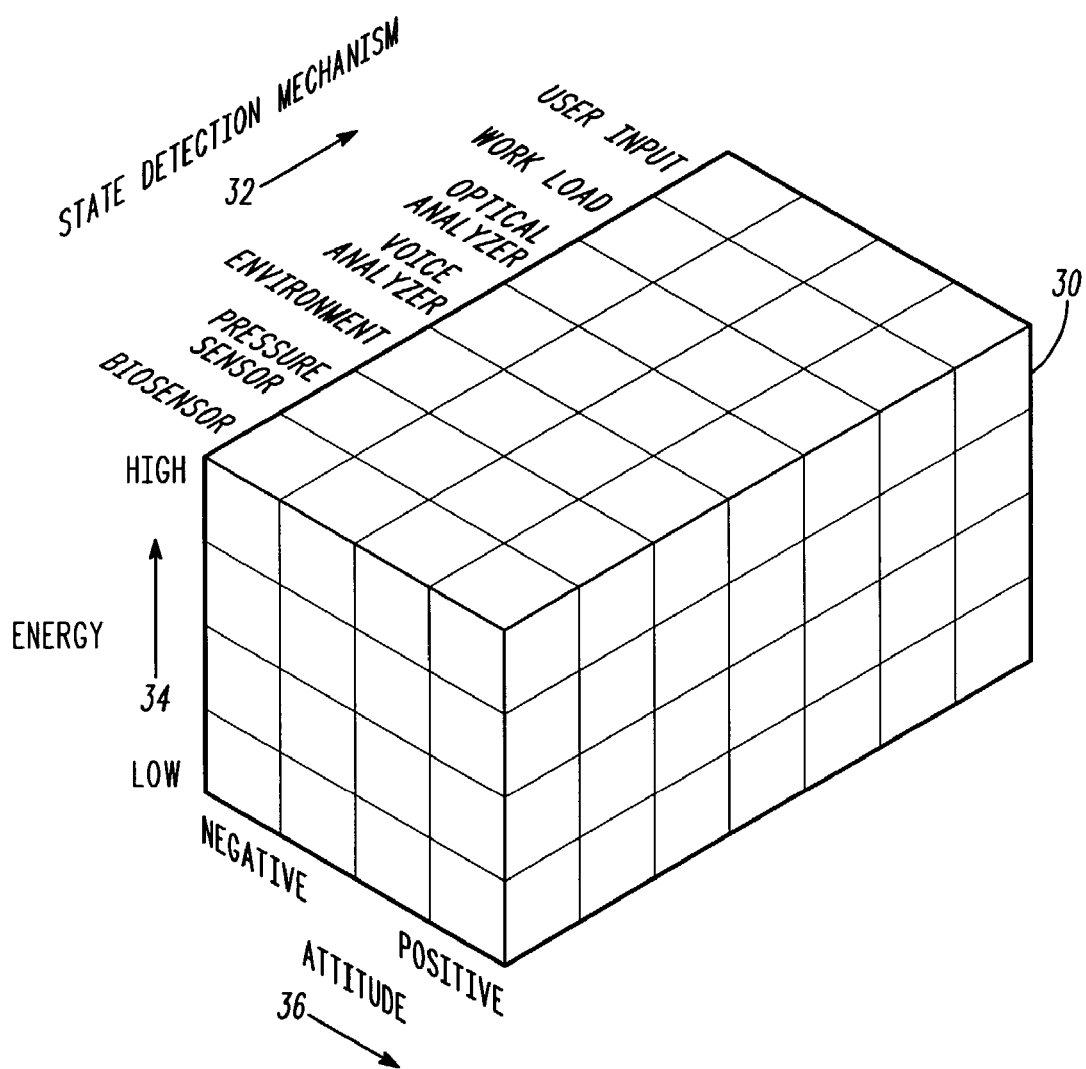
FIG. 3 shows a graphical representation of a matrix of emotional and physiological state attributes, in accordance with the present invention.

Referring to FIGS. 2 and 3, the interpretation of the signal 25 into state data 23 can be accomplished by providing a memory 27 coupled to the controller. The memory 27 and storage buffer 24 can be the same device. Moreover, the memory and storage buffer can be part of the controller 22. For example, the controller 22 can contain a processor and memory management unit (MMU) of an application specific integrated circuit (ASIC). The memory 27 includes a table of possible input device signals and emotional and physiological state data corresponding thereto. The controller 22 maps the signal to the table to identify the corresponding emotional or physiological state.

FIG. 3 illustrates an example of a data structure of a particular user's emotional and physiological states stored in attribute cells of the memory of the recipient communication device. Each user's set of emotional and physiological states can be stored as a multi-dimensional matrix 30 as illustrated by the exemplary three-dimensional matrix of FIG. 3. The three-dimensional matrix is structured along three axes: an input mode axis 32, an energy level axis 34, and a state axis 36. The three axes define an attribute cell with a code that can be read by a sender of information defining an emotional and/or physiological state of a recipient of the information.

The input mode axis 32 of the matrix is classified by various types of user interface modes that can be used as metrics for measuring an emotional or physiological state of a user. Examples of these are biosensors, pressure sensors, voice analyzers, environment, workload schedule or user input. These categories correspond essentially to the biological activity, environmental activity, or context of a human user. The illustrated categories are by example only and various categories and subcategories of attributes can be used depending on the level of state sensitivity desired by the system or by a particular communication sender of the system.

The energy level axis 34 is used to define the amount of emotional or physiological activity by a user. A low emotional or physiological activity would indicate that the user is calm. A high emotional or physiological activity would indicated that the user is intense. However, intensity can be indicated with a happy state or a sad state, which is not indicated on the energy level axis.

The state axis 36 defines whether the indicated emotions are positive (good) or negative (bad). In relation with the energy level axis 34, the low energy, negative state can be indicative of a depressed emotional state. A high energy, negative state can be indicative of an angry emotional state or overworked physiological state. In contrast, a low energy, positive state can be indicative of a content emotional state. A high energy, positive state can be indicative of a happy emotional state. The number of divisions of each axis defines the sensitivity required. Four levels are shown on the energy level axis and state axis as an example. The number of levels can be dynamically allocated or set per predetermined conditions.

In the biosensor category, the biosensor can monitor the pulse or heart rate of a user, for example. A low pulse would be indicative of a low energy level or a calm state, which is directly correlated on the energy level axis. Correspondingly, a higher pulse rate would be indicative of a high energy level or a stressed state. The biosensor can also be used to monitor any of the physiological states of the user and is only limited by the technology available in biosensors. For example, skin conductivity, body chemistry, brain activity (alpha, theta, beta waves), and the like can all be used in this manner.

In the pressure sensor category, the sensor can detect how hard the user is holding the cellular telephone. A lower pressure would be indicative of a low energy level or a calm state, which is directly correlated on the energy level axis. A higher pressure would be indicative of a high energy level or a stressed state. This can be either an involuntary or a voluntary situation, e.g. subconscious tensing or intentional squeezing could convey affection.

In the environment category, the environment of the user can be detected through various sensors or techniques. For example, noise level can be detected through a microphone of the device. Temperature can also be detected through the temperature compensation circuits of the telephone. Location or motion can also be used in those devices having location technology such as Global Positioning System (GPS). Lighting could also be detected in those devices equipped with video circuitry. A high noise, extreme temperature, high light, busy location or high motion can be indicative of a high energy environment proportional to a stressed physiology of a user, which is directly correlated on the energy level axis. A low noise, normal temperature, low light, rural or stationary location or can be indicative of a low energy environment proportional to a calm physiology of a user.

In the voice analyzer category, the processor of the device can be used to analyze the voice of the user and dynamically provide the emotional or physiological state of the user. Rapid speech or speech with stress can be indicative of a high energy, which is directly correlated on the energy level axis. Slow or low stress speech would be indicative of a low energy level of the user.

In the optical analyzer category, video circuits can detect rapid or shifting background, movement of the user, or of parts of the user such as hands, arms or eyes, which can be indicative of a high energy level correlated on the energy level axis. Little motion on the part of the user or background would be indicative of a low energy physiology of the user. Optionally, a change in motion or rapidity of motion can be correlated to energy.

In the workload category, a physical parameter of the user is not involved. A download of the user's schedule or itinerary can be indicative of a probable physiological state of the user. A heavy workload or busy itinerary at a particular time of communication can be indicative of a high energy level correlated on the energy level axis. A small workload or calm period in a calm itinerary at a particular time of communication would be indicative of a low energy level.

In the user input category, the user can intervene and directly provide an emotional or physiological state manually, instead of using the automatic functions described above, to control the interface mode or format of any information to be received.

All of the above categories can be interactive to provide data on the state axis. For example, the voice analyzer can be used not only to recognize speed or stress of speech, but actual words can be recognized that relate to attitude. Along these lines, the optical analyzer can detect smiles or frowns. Workload is likely to have a direct correlation between energy and attitude barring any other external influence, i.e. less workload equates to happier outlook in the matrix. Similarly, a calmer environment would relate to happier attitude. Of course, user input would be most reliable and would have priority.

A code representing a user's attitude and energy level is stored in each attribute cell located at the intersection of the matrix's different axes of access. The code can be averaged (with or without weighting or other statistical function) along the input mode axis 32 to obtain a reasonable value for the user's emotional or physiological state. In particular, a state data vector can be derived by the recipient device based on the emotional and physiological state of the recipient. The state data vector thus can represent axes of matrix of attributes. For example, an environment code indicative of emotional attributes can be used for the vector, expressed as {energy, attitude}. The vector can be further defined by the type of communication preference, such as visual and audible human preferences, expressed as {environment, {visual, audible}}. Optionally, the vector can contain a user code for the particular user sharing the device. A user code would not be needed in those devices using removable smart cards, for example, specific to a single user. In such an instance, user information does not need to be sent to the smart card because the card provides preference information for only one user. In any of the above conditions, the communication device of a sender of information or originator of a call would receive the code or vector before commencement of communication with a recipient, and alter communication mode or format accordingly.

For example, if it is found that a recipient is in a noisy environment and is agitated and in a negative mood, a sender would be notified by his communication device that it has chosen to send a text message instead of a voice message, mitigating the noise problem, in a text format such as SMS in order not to aggravate the recipient. This can be done either automatically or manually by the user. The sender can also choose to defer sending of the message and monitor the recipient until their mood or circumstances improve. As another example, if a user is in a quiet environment and is calm and positive, or if the location shows the user is in a public place, than a sender's communication device can choose to send a text message instead of a voice message, to not agitate, disturb or embarrass the user, and possibly place the call using a non-audible ringing of a cellular telephone using a vibrator, for example.

Attributes on the energy/attitude plane should be substantially uniform through the matrix 30 along the mode axis 32. It should be recognized that more than three axes can be used besides the three axes shown. Alternatively, the energy axis 34 and attitude axis 36 can be combined into a simpler two-dimensional implementation of the matrix 30. In either case, the controller of the device constantly presents an attribute code representing emotional and physiological state data of the recipient to the storage buffer for retrieval by a sending device. Once the state data is received by the sending device, the communication can be adapted for the recipient accordingly. In devices not equipped in accordance with the present invention, a neutral or default state data value can be assumed by the sender.

In another embodiment, and referring back to FIG. 2, the controller 22 can interpolate emotional and physiological state data to provide a more refined and sensitive state of the user. Preferably, the sending communication device includes a learning mode, wherein the sending communication device adapts its communication to the recipient communication device to match previous communications therewith. In particular, the apparatus can store and predict states. For example, a layered neural network can serve as both a memory to store states and as a processor to predict states. The neural network operates to provide predicted states in relation to a code or vector from the recipient device. The neural network can also serve to learn states in relation to a code or vector. The neural network can learn based on weight values imparted on individual emotional of physiological attributes or correlation factors between attributes. In this case, a weight error algorithm, such as can be accomplished by a comparator, can provide the weights based on a difference between outputs of the neural network and the attributes for an associated vector input.

More preferably, the sending device can include a predictive mode for states of a recipient. The prediction procedure can predict states by access or interpolation to the next best attribute stored in adjacent attribute cells of the matrix. The attributes can be accurately determined using artificial intelligence. Alternatively, fuzzy logic can be used to predict the attributes. Furthermore, the attributes can be predicted by a neutral network used to learn a user's preferences for various times, environments and the like. The prediction procedure can be performed either in the sending or recipient communication device. The prediction procedure can be performed based on the states contained in the recipient communication device, such as those attributes in the matrix.

A user can also use a refinement process that allows the user to customize predicted states, and allows the user to identify unique preferences for the attributes the user wishes to refine. The user can also define a selection of attributes not previously encountered. Such customization or selection can be from a list of choices or defaults based on historical data, such as the information received from a recipient device. The choices preferably represent various predicted states ranked in likelihood of correctness by the prediction process.

In another embodiment, the sending communication device includes a group call mode for members of the group having a recipient communication device capable of determining an emotional or physiological state of each member. In this case, the sending communication device can display a visual indicator, such as au emoticon for each member in the group demonstrating their emotional or physiological state and changes thereto during the commumication.

Figure 4:
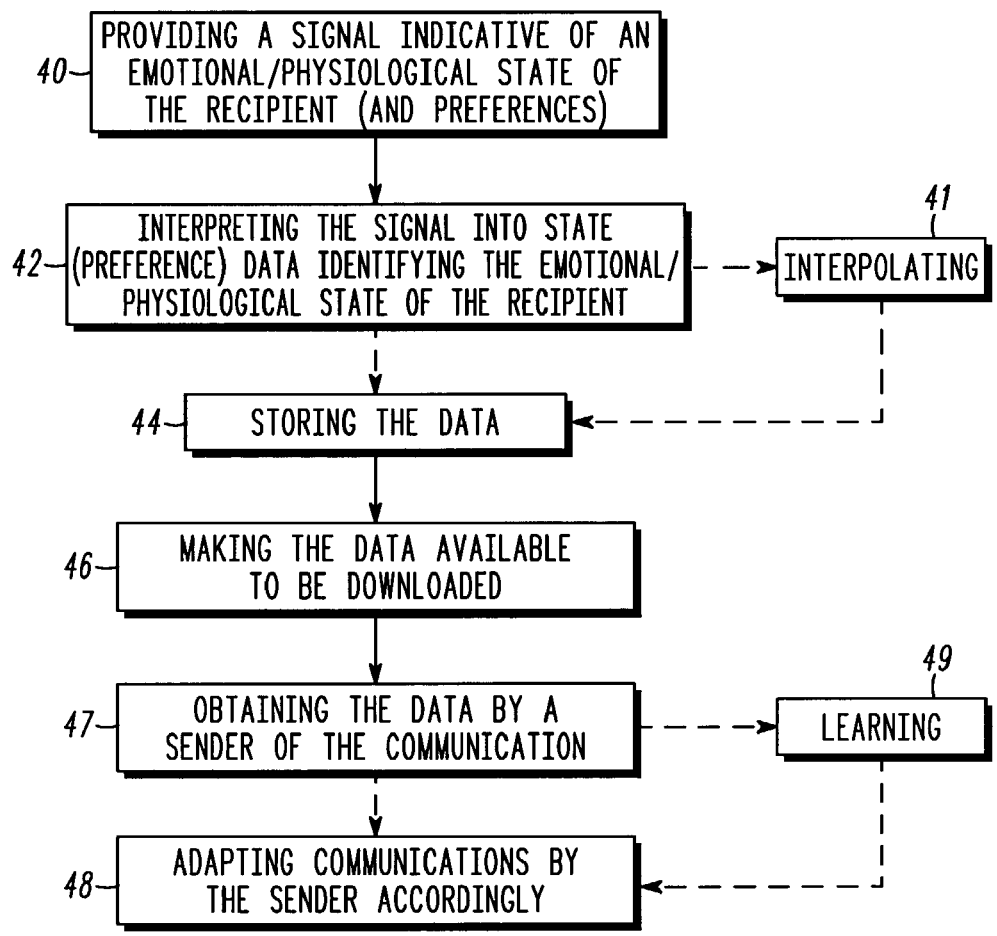
FIG. 4 shows a flow chart of a method for determining the emotional and physiological state of a recipient of a communication, in accordance with the present invention.

FIG. 4 illustrates a method for determining emotional and physiological states of a recipient of a communication. In its simplest form, the method includes a first step of providing 40 a signal indicative of one of an emotional and a physiological state of the recipient. Preferably, this is done dynamically to keep the state updated. The providing step is accomplished through an input device comprising the various sensors previously described including any other devices that provide a signal indicative of sensory input. Optionally, communication preferences can be defined and provided. A next step includes interpreting 42 the signal into state data identifying one of an emotional and a physiological state of the recipient. Interpretation can include using the signal as is, or mapping the signal to a corresponding set of emotional or physiological state values, in a memory table for example. A next step includes storing 44 the state data. A next step includes making 46 the state data available to be downloaded.

In practice, the state data is predetermined in a (recipient) communication device such that the communication device of a sender of a communication can obtain 47 the state data and adapt 48 the communication to the recipient accordingly, and as described above. For example, an interface mode or communication protocol of the communication can be changed to suit the emotional and a physiological state of the recipient. In general, the emotional and a physiological state can be characterized as one or more of a biological process of the recipient, an environment of the recipient, and a context of the recipient, as previously described. The sender can then have their own set of predetermined preferences as to how to communicate with a particular recipient when they are in any particular state. Therefore, the sending device can automatically configure the communication to suit the recipient's state using the sender preferences, or the sender can manually change formats or protocols to suit the situation.

In a preferred embodiment, a step of learning 49 is used by a sender of a communication to match a mode of communication with previous communications associated with particular state data of a recipient. This improves communication efficiency. In addition, a step of interpolating 41 can be added to increase the sensitivity of the signal of the providing step, further optimizing communication quality and effectiveness.

Figure 5:
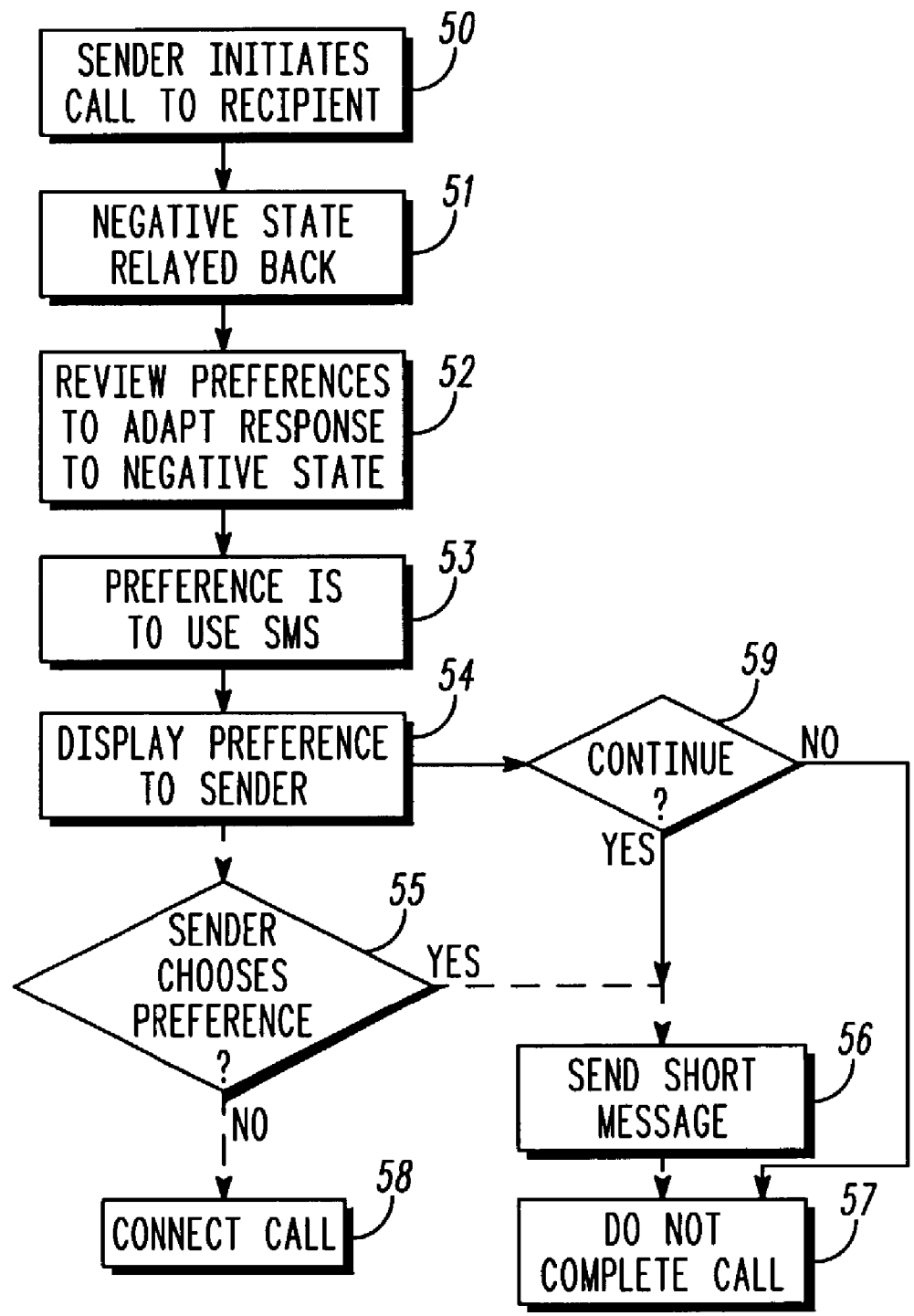
FIG. 5 illustrates a first exemplary application of the present invention.

FIG. 5 shows a first example of an application of the present invention. A first user (sender) initiates 50 a call to a second user's (recipient) cellular phone. A preliminary connection is made to the recipient phone and a negative emotional or physiological state is sent back 51 (using the methodology of FIG. 4) through the network to the sender's phone before the call is put through. Through a set of predefined preferences 52, the sender's communication device only provides minimal information 53 when the recipient is in a bad mood. Therefore, the sender's phone, in accordance with the predefined preferences, automatically switches into Short Message Service (SMS) mode and displays 54 this preference to the user. The sender getting this prompt 54 realizes that a short message is called for and chooses 59 whether to send 56 such short message by speaking or typing a short message to be sent to the recipient 56, or the user can elect to terminate the call 57. In this way, the sender's device selects the method and mode for communication and gives the sender the choice to complete the call or not.

Optionally, after the sender's phone determines 53 that the communication preference is Short Message Service (SMS) and prompts 54 the sender, the sender can choose 55 whether to send 56 such short message without completing the voice call connection 57 that would initiate voice communication with the recipient, or to go ahead and connect 58 the call to talk to the recipient directly.

Figure 6:
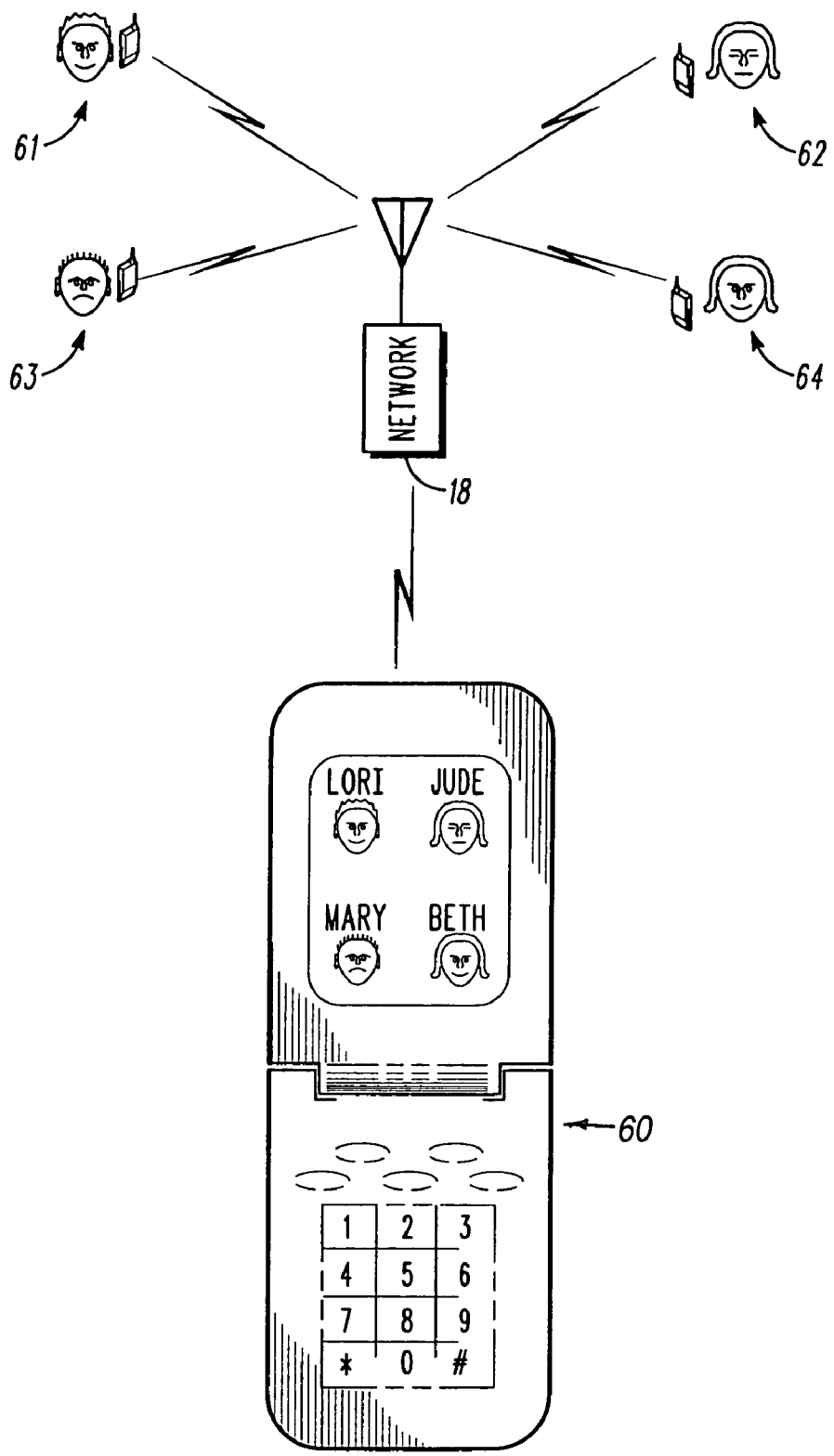
FIG. 6 illustrates a second exemplary application of the present invention.

FIG. 6 shows a second example of a dynamic group call of the present invention. A user of device 60 wishes to know the emotional of physiological states of a group of friends 61, 62, 63, 64. These emotional states are communicated through the network 18 to the device 60, in accordance with the present invention. The actual communication can be an active group call with the friends 61, 62, 63, 64, or can be a passively monitoring of emotional states of the friends through GSM Short Messaging Service, for example. The emotional states of the friends can be translated and displayed on the device 60 as representative emoticons, text, sound or other techniques. In such a group situation, the various people's emotional states can be displayed, and preferably monitored for change in emotional state that would indicate a need for comment, intervening or communication on the part of the user of the device 60 to the person whose emotional state has changed. In other words, if a monitored emotional state of person 63, Lori, shows a marked negative change, then the user could be alerted by the device, or take action on their own, to contact and console Lori. Similarly, if a monitored emotional state of person 64, Beth, shows a marked positive change, then the user could be alerted by the device, or take action on their own, to contact and congratulate Beth. The alert can be passive or active and can include an audio alert, tone or vibration to indicate an emotional change in one of the people being monitored. In either event, personal preferences can provide the appropriate mode that a sender or recipient prefers to control these kinds of interactions, given a specific emotional or physiological characteristic.

Although the invention has been described and illustrated in the above description and drawings, it is understood that this description is by example only and that numerous changes and modifications can be made by those skilled in the art without departing from the broad scope of the invention.

What is claimed is:

1. A communication system comprising:
    a first communication device including:
        an input device operable to receive at least one signal indicative of an emotional or physiological state of a user of the first communication device,
        a first processing unit coupled to the input device, the first processing unit operable to receive the at least one signal from the input device, interpret the at least one signal into state data indicating an emotional or a physiological state of the user of the first communication device, and at least temporarily store the state data, and
        a first transmitter coupled to the first processing unit and operable to transmit the state data; and
    a second communication device including:
        a receiver operable to receive the state data from the first communication device;
        a second processing unit coupled to the receiver and selectively supporting a plurality of communication modes for the second communication device, the second processing unit being operable to automatically select a communication mode of the plurality of communication modes with which to send a communication to the first communication device based on the received state data so as to take into account the emotional or physiological state of the user of the first communication device, the second processing unit being further operable to compare the selected communication mode with a current communication mode of the second communication device and, when the selected communication mode is different than the current communication mode, automatically change the current communication mode of the second communication device to the selected communication mode, and
        a second transmitter coupled to the second processing unit and operable to transmit the communication to the first communication device in accordance with the selected communication mode.

2. The system of claim 1, wherein the first processing unit is operable to interpolate stored state data to refine a determination of the emotional or a physiological state of the user of the first communication device.

3. The system of claim 1, wherein the second communication device includes a learning mode in which the second communication device is operable to adapt a communication to the first communication device to match previous communications with the first communication device taking into account the emotional or physiological state of the user of the first communication device.

4. The system of claim 1, wherein the second communication device adapts information by changing an interface mode of the second communication device.

5. The system of claim 1, wherein the input device monitors one or more of the group consisting of a biological process of the user of the first communication device, an environment of the user of the first communication device, and a context of the user of the first communication device.

6. The system of claim 1, further comprising:
    a memory coupled to the first processing unit, the memory having a table of possible input device signals and emotional and physiological state data corresponding thereto, wherein the first processing unit maps the at least one signal to the table to identify the emotional or physiological state of the user of the first communication device.

7. The communication system of claim 1, wherein the first communication device includes a memory that stores a multi-dimensional matrix having a plurality of attribute cells containing codes corresponding to possible emotional or physiological states of the user of the first communication device, and wherein the first processing unit is further operable to determine an emotional or physiological state of the user of the first communication device by using interpolation to select an attribute cell of the plurality of attribute cells based at least on the at least one signal.

8. The system of claim 1, further comprising:
    at least a third communication device including:
        a second input device operable to receive at least a second signal indicative of an emotional or physiological state of a user of the third communication device,
        a third processing unit coupled to the second input device, the third processing unit operable to receive the at least a second signal from the second input device and interpret the at least a second signal into third device state data indicating an emotional or a physiological state of the user of the third communication device, and
        a third transmitter coupled to the third processing unit and operable to transmit the third device state data;
    wherein the first communication device and the at least a third communication device constitute a group of communication devices which are independently capable of determining emotional or physiological states of respective users of the first communication device and the at least a third communication device;
    wherein the receiver of the second communication device is further operable to receive the third device state data from the third communication device; and
    wherein the second communication device further includes a group call mode in which the second communication device displays a first visual indicator representative of the user of the first communication device and a second visual indicator representative of the user of the third communication device, the first visual indicator demonstrating the emotional or physiological state of the user of the first communication device based on the state data and the second visual indicator demonstrating the emotional or physiological state of the user of the third communication device based on the third device state data.

9. The system of claim 1, wherein said first processing unit acts autonomously to obtain the at least one signal and determine the state data.

10. The system of claim 1, wherein the input device includes a user interface of the first communication device, and wherein the user interface is operable to at least allow the user of the first communication device to define communication preferences associated with different emotional or physiological states.

11. A communication device operable to adapt a communication intended for a user of a target communication device to an emotional or physiological state of the user of the target communication device, the communication device comprising:
- a receiver operable to receive, from the target communication device, data indicating an emotional or physiological state of the user of the target communication device;
- a processing unit coupled to the receiver and selectively supporting a plurality of communication modes for the communication device, the processing unit being operable to automatically select a communication mode of the plurality of communication modes in which to send the communication to the target communication device based upon the received data so as to take into account the emotional or physiological state of the user of the target communication device, the processing unit being further operable to compare the selected communication mode with a current communication mode of the communication device and, when the selected communication mode is different than the current communication mode, automatically change the current communication mode of the communication device to the selected communication mode; and
- a transmitter coupled to the processing unit, the transmitter operable to transmit the communication to the target communication device in accordance with the selected communication mode.

12. The communication device of claim 11, wherein the processing unit automatically changes the current communication mode to the selected communication mode by at least one of changing the format of the communication, changing the communication protocol, and changing the interface mode.

13. The communication device of claim 11, wherein the processing unit is further operable to predict an emotional or physiological state of the user of the target communication device in connection with a subsequent communication occurring at some time after the communication based upon data corresponding to emotional or physiological states of the user of the target communication device that was received in connection with one or more previous communications and without receiving data corresponding to the emotional or physiological state of the user of the target communication device in connection with the subsequent communication.

14. The communication device of claim 11, wherein the communication device is operable to adapt communications intended for users of a group of communication devices to emotional or physiological states of the users of the group of communication devices, wherein the group of communication devices includes the target communication device and at least one other target communication device, wherein the receiver is further operable to receive, from the at least one other target communication device, data indicating an emotional or physiological state of a user of the at least one other target communication device, wherein the processing unit further supports a group call mode in which the communication device displays a first visual indicator representative of the user of the target communication device and at least a second visual indicator representative of a user of the other target communication device, the first visual indicator demonstrating the emotional or physiological state of the user of the target communication device based on the received data indicating the emotional or physiological state of the user of the target communication device and the second visual indicator demonstrating the emotional or physiological state of the user of the other target communication device based on the received data indicating the emotional or physiological state of the user of the other target communication device.

15. A method for a first communication device to send a communication to a second communication device so as to take into account an emotional or physiological state of a user of the second communication device, the first communication device being operable in a plurality of communication modes, the method comprising:
- receiving, from the second communication device, data indicative of the emotional or physiological state of the user of the second communication device;
- automatically selecting a communication mode of the plurality of communication modes in which to send the communication to the second communication device based on the received data so as to take into account the emotional or physiological state of the user of the second communication device;
- determining whether the selected communication mode matches a current communication mode of the first communication device;
- automatically altering the current communication mode of the first communication device to the selected communication mode if the selected communication mode does not match the current communication mode; and
- transmitting the communication to the second communication device in accordance with the selected communication mode.

16. The method of claim 15, wherein the automatically selecting step further comprises:
- mapping the received data to a table identifying possible emotional or physiological states of the user of the second communication device; and
- determining the emotional or physiological state of the user of the second communication device from the table.

17. The method of claim 15, wherein the automatically selecting step further includes comparing the received data to defined communication preferences.

18. The method of claim 15, wherein the automatically selecting step further includes interpolating the received data and previously received data indicative of prior emotional or physiological states of the user of the second communication device to determine the emotional or physiological state of the user of the second communication device.

19. The method of claim 15, wherein the automatically selecting step further includes predicting the emotional or physiological state of the user of the second communication device based on the received data and previously received data indicative of prior emotional or physiological states of the user of the second communication device.

20. The method of claim 15, wherein the selected communication mode includes an interface mode for the communication.

21. The method of claim 15, wherein the step of automatically altering the current communication mode of the first communication device to the selected communication mode includes:
- at least one of changing a format of the communication and changing a communication protocol.

22. A communication device operable to adapt a communication intended for a user of a target communication device to an emotional or physiological state of the user of the target communication device, the communication device comprising:
  a receiver operable to receive, from the target communication device, data indicating an emotional or physiological state of the user of the target communication device;
  a processing unit coupled to the receiver and operable to automatically select a mode for communicating with the target communication device based on the received data and a set of predefined preferences so as to take into account the emotional or physiological state of the user of the target communication device, wherein the set of predefined preferences defines how the communication device is to communicate with the target communication device based on the emotional or physiological state of the user of the target communication device and causes the processing unit to automatically change at least one of a format, a protocol, and an interface mode of the communication to suit the emotional or physiological state of the user of the target communication device; and
  a transmitter coupled to the processing unit, the transmitter operable to transmit the communication to the target communication device in accordance with the selected mode for communicating.

* * * * *